US012806345B2

(12) United States Patent
Malviya et al.

(10) Patent No.: US 12,806,345 B2
(45) Date of Patent: Nov. 24, 2026

(54) ANESTHESIA SAFETY NEEDLE DEVICE

(71) Applicant: Becton, Dickinson and Company, Franklin Lakes, NJ (US)

(72) Inventors: Rahul Malviya, Bangalore (IN); Amarsinh Deeliprao Jadhav, Bangalore (IN); Praveen Nalawade, Bangalore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 989 days.

(21) Appl. No.: 17/893,444

(22) Filed: Aug. 23, 2022

(65) Prior Publication Data

US 2023/0072001 A1 Mar. 9, 2023

Related U.S. Application Data

(60) Provisional application No. 63/241,263, filed on Sep. 7, 2021.

(51) Int. Cl.
*A61M 5/32* (2006.01)
*A61M 19/00* (2006.01)

(52) U.S. Cl.
CPC .......... *A61M 5/3213* (2013.01); *A61M 19/00* (2013.01); *A61M 2005/3215* (2013.01)

(58) Field of Classification Search
CPC . A61M 5/3216; A61M 25/0631; A61M 19/00
See application file for complete search history.

(56) References Cited

U.S. PATENT DOCUMENTS

| | | | | |
|---|---|---|---|---|
| 4,664,259 | A | 5/1987 | Landis | |
| 4,820,277 | A | 4/1989 | Norelli | |
| 5,011,479 | A * | 4/1991 | Le | A61M 5/3271 604/263 |
| 5,147,319 | A | 9/1992 | Ishikawa et al. | |
| 5,693,022 | A | 12/1997 | Haynes | |
| 5,746,727 | A * | 5/1998 | Graves | A61M 25/0631 604/533 |
| 5,919,172 | A * | 7/1999 | Golba, Jr. | A61B 17/3401 604/231 |
| 6,413,243 | B1 | 7/2002 | Geist | |
| 2015/0151054 | A1 | 6/2015 | Wilkinson | |
| 2015/0352291 | A1* | 12/2015 | Fournier | A61M 5/3216 604/197 |

FOREIGN PATENT DOCUMENTS

GB 2239604 A 7/1997

OTHER PUBLICATIONS

PCT Invitation to Pay Additional Fees in PCT/US2022/041298 dated Nov. 10, 2022, 13 pages.
PCT International Search Report and Written Opinion in PCT/US2022/041298 dated Jan. 30, 2023, 22 pages.

* cited by examiner

*Primary Examiner* — Emily L Schmidt
(74) *Attorney, Agent, or Firm* — SERVILLA WHITNEY LLC

(57) ABSTRACT

Needle covers having a clam-shell configuration configured to removably attach to a feature of a needle while the needle is inserted into the skin of a patient. The needle cover comprises a base having connecting feature, and a two-piece hinged cap connected to the base by two living hinges.

15 Claims, 12 Drawing Sheets

ANESTHESIA SAFETY NEEDLE DEVICE

CROSS-REFERENCE TO RELATED APPLICATIONS

This application claims priority under 35 U.S.C. § 119(e) to U.S. Provisional Application No. 63/241,263, filed Sep. 7, 2021, the disclosures of which are incorporated herein by reference in their entirety.

TECHNICAL FIELD

The present disclosure relates to safety needle device covers, and in particular the present disclosure relates to clam-shell needle sleeves and covers for needles and introducer needles.

BACKGROUND

It is estimated that 600,000 to 800,000 needlestick injuries occur per year in the United States. Vascular Access Devices (VAD) are used throughout the medical industry for the injection and withdrawal of a wide variety of fluids and solutions into and from the human body. Because of the numerous potential hazards associated with the handling and manipulation of bodily fluids, particularly blood, there are a number of known safety features that are frequently incorporated into various types of needle devices to protect the practitioner from accidental exposure to the needle. Needlesticks are a common occurrence in the health care profession.

Conventional vascular access devices are retrieved from a blister package, the needle shield is removed and then the plastic hub is attached to a luer lock or luer slip syringe. Drug from a vial is then retrieved and administered to the patient via injection. In spinal applications such as spinal anesthesia where there is an introducer needle and a spinal needle that are withdrawn together, once the anesthesia drug delivery is completed, the needle assembly is withdrawn from body and disposed without putting the needle shield back in place which can result in needlestick injury or cross contamination. The needle is then discarded either as is or after capping, both methods carrying their own risks of injury or contamination. On the other hand, a safety needle has an extra step wherein an additional component, the safety shield, is deployed to permanently "engulf" the needle thereby making it inaccessible. This ensures that the needle cannot be reused and also contributes to healthcare worker safety—by protecting them from contaminated needle stick injury. This extra step of safety needles are enabled by either a unique hub design that acts as a base for the safety mechanism to attach onto or a very complicated safety shield mechanism.

Thus, there is a need to provide a cover and needle shield for vascular access devices and spinal anesthesia needle assemblies incorporating features that reduce needle stick injuries while reducing manufacturing costs, including materials and molding complexity. Furthermore, there is a need to provide a method for removing a vascular access device and spinal anesthesia needle which reduces needle stick injuries.

SUMMARY

A first aspect of the present disclosure relates to a needle cover device having a base and a two-piece hinged cap. The base has a rectangular shape and a connecting feature, the connecting feature configured to removably interdigitate with a feature of a needle hub. The two-piece hinged cap is connected to the base by two living hinges, the two-piece hinged cap having a proximal surface and a distal surface, the two-piece hinged cap having a rectangular medial portion forming a cavity configured to enclose at least the needle hub within. Each of the two-piece hinged cap has a rectangular medial portion and a lateral portion, the medial portion having a rectangular cavity formed on the distal surface configured to accommodate the needle hub, and the lateral portion having a cavity configured to accommodate a needle cannula.

In some embodiments, the connecting feature of the base comprises a pair of teeth forming a channel, the pair of teeth and channel configured to interdigitate with a flange of the needle hub. In some embodiments, the pair of teeth have a u-shaped cross-section which can be sized and dimensioned to accommodate the flange of the needle hub.

In some embodiments, the two-piece hinged cap is configured to pivot at least 180 degrees around each of the two living hinges from an open position to a closed position, wherein each distal surface of each two-piece hinged cap is closed onto the other in the closed position.

In some embodiments, each of the living hinges extend an entire width of the rectangular shape of the medial portion.

In some embodiments, the medial portion is configured to cover and accommodate an assembled spinal anesthesia introducer needle hub and spinal needle hub. In some embodiments, the connecting feature connects to a flange of the spinal needle hub. In some embodiments, the rectangular cavity has a length $L_F$ extending from the flange of the spinal needle hub slightly past the distal end of the introducer needle hub such that the introducer needle hub and spinal needle hub are fully enclosed within the rectangular cavity.

In some embodiments, the connecting feature is configured to attach to a flange of the needle hub by sliding the foldable needle cover in a medial direction relative to the needle hub.

In some embodiments, the medial portion further includes a winged tab extending from the proximal surface configured to provide a surface area for manipulating and closing the two-piece hinged cap.

In some embodiments, distal edges of the lateral portion of each of the two-piece hinged cap are configured to interlock with one another in a snap-fit configuration.

In some embodiments, the foldable needle cover is injection molded forming a singular unitary body.

A second aspect of the present disclosure is directed to method of covering a spinal-introducer needle assembly. The method comprises the steps of sliding a foldable needle cover in a medial direction relative to a syringe assembly over a spinal-introducer needle assembly; withdrawing the spinal-introducer needle assembly and syringe assembly while the foldable needle cover is attached to the spinal-introducer needle assembly; and, closing the foldable needle cover over the spinal-introducer needle assembly.

In some embodiments, the foldable needle cover is slidable over the spinal-introducer needle assembly while the spinal-introducer needle assembly is still at least partially inserted within a patient.

In some embodiments, the foldable needle cover is closed over the spinal-introducer needle assembly by depressing winged tabs located on a two-piece hinged cap of the foldable needle cover, the two-piece hinged cap connected to a base of the foldable needle cover by two living hinges. In some embodiments, depressing the winged tabs causes the two-piece hinged cap to pivot on the two living hinges.

In some embodiments, the spinal-introducer needle assembly and syringe assembly 90 are withdrawn with one hand from the skin of a patient while the foldable needle cover is attached to the spinal-introducer needle assembly.

In some embodiments, the spinal-introducer needle assembly is withdrawn while closing the foldable needle cover over the spinal-introducer needle assembly simultaneously.

A second aspect of the present disclosure is directed to a safety needle devise assembly comprising an introducer needle, a two-piece hinged cap and a sliding block. The introducer needle has an introducer needle hub and an introducer needle cannula extending from a distal end of the introducer needle hub, the introducer needle hub having a pair of attachment points positioned at the distal end of the introducer needle hub. The two-piece hinged cap has an elongated body connected to the pair of attachment points a pair of corresponding attachment points located on a medial portion of the two-piece hinged cap, the two-piece hinged cap having a proximal surface and a distal surface, the distal surface having a cavity configured to enclose at least the introducer needle cannula within, each medial portion including a tab extending from the proximal surface. The sliding block is configured to open or close the two-piece hinged cap, the sliding block having a proximal wall, a distal wall and a sidewall therebetween defining a cavity, the distal wall configured to abut the tabs of the two-piece hinged cap.

In some embodiments, the assembly further comprises a spinal needle connected to the introducer needle.

In some embodiments, the attachment points of the introducer needle hub create a snap connection with the pair of corresponding attachment points of the two-piece hinged cap.

In some embodiments, introducer needle hub further comprising a pair of wings extending from an outside surface of the introducer needle hub, the pair of wings having a width greater than a width of an opening of the proximal wall of the sliding block.

In some embodiments, the pair of wings are configured to interdigitate with a channel formed on an inside surface of the side wall of the sliding block.

In some embodiments, the proximal wall of the sliding block is removable from the sliding block. In some embodiments, the distal wall is against the tabs of the two-piece hinged cap. In some embodiments, the distal wall of the sliding block is against the tabs of the two-piece hinged cap.

In some embodiments, movement of the sliding block in a proximal direction causes the two-piece hinged cap to pivot about the attachment points of the introducer needle hub causing the two-piece hinged cap to open from a closed position to an open position

DETAILED DESCRIPTION

Figure 1A:
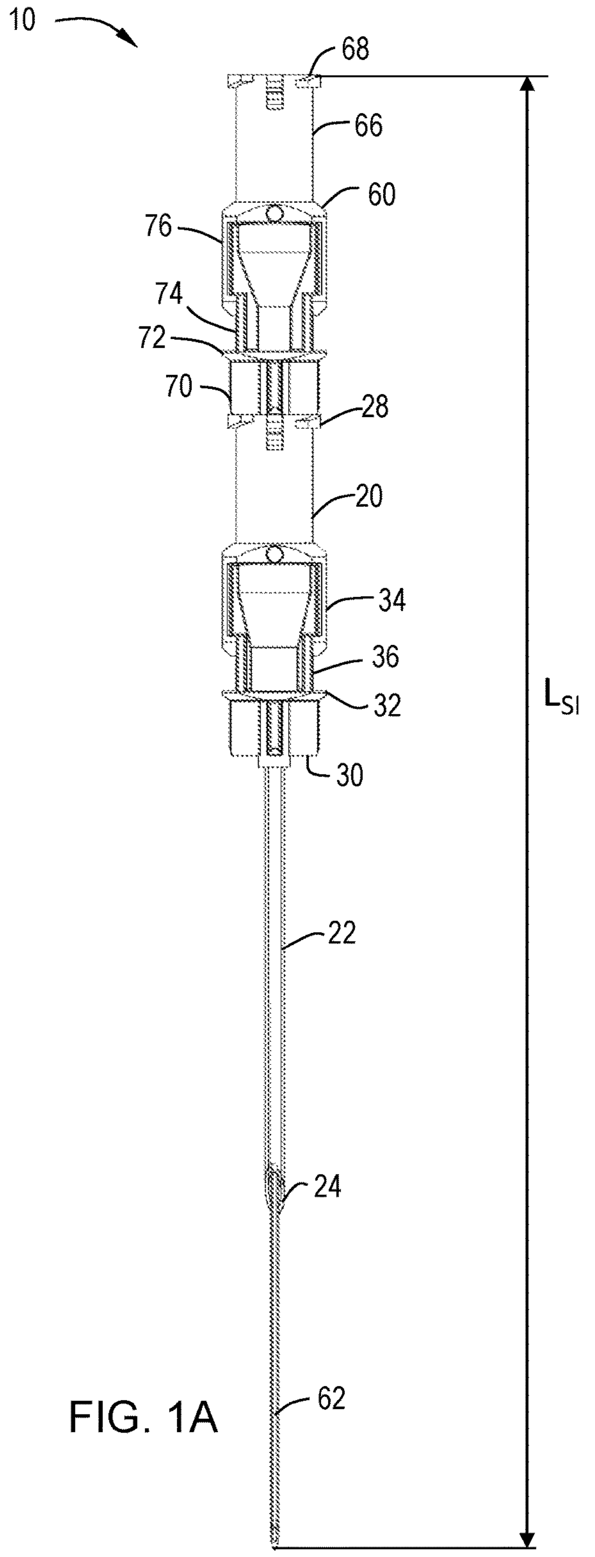
FIG. 1A illustrates a side view of a spinal-introducer needle assembly in accordance with one or more embodiments of the present disclosure.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "proximal", "distal", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of one or more interlocking tubes, slightly tapered to hold together with just a simple pressure/twist fit/friction fit. Luer connectors can optionally include an additional outer rim of threading, allowing them to be more secure. The Luer connector can interlock and connect to the end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe. As used herein, the term “Luer connector” refers to a male luer connector or a female luer connector.

As used herein, the term “medical device” refers to common medical devices having threaded or interlocking connections, the connections having corresponding mating elements. By way of example but not limitation, a syringe may have a threaded connection which releasably interlocks with a secondary medical device such as a needless connector of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as “thread”, “taper”, “tab”, “wall”, “proximal”, “side”, “distal” and others are used throughout this specification to facilitate understanding, it is not intended to limit any components that can be used in combinations or individually to implement various aspects of the embodiments of the present disclosure.

Embodiments of the present disclosure are directed to foldable needle sleeves and covers having a clam-shell configuration. The foldable needle cover of the embodiments described are configured to removably attach to a feature of a needle hub. By way of example but not limitation, the foldable needle cover can be configured to removably attach to a flange, ledge or taper of a needle hub. The needle hubs, needles and cannulas described herein can be conventional in the art or can include non-standard or novel features. In further embodiments described herein, a needle hub is configured to include pivot points for a two-piece hinged cap. In further embodiments, a slider is configured to cover at least part of the pivot points thereby preventing opening of the two-piece hinged cap.

Embodiments of the foldable needle covers disclosed herein and shown in FIGS. 1 through 6D attach to a spinal-introducer needle assembly 10. The foldable needle cover 100 is capable of attachment to the spinal-introducer needle assembly 10 while the spinal-introducer needle assembly 10 is still inserted into the skin of a patient. As the spinal-introducer needle assembly 10 is withdrawn, the foldable needle cover 100 can be closed and securely cover the spinal-introducer needle assembly 10, thereby preventing needle stick injuries.

Figure 1B:
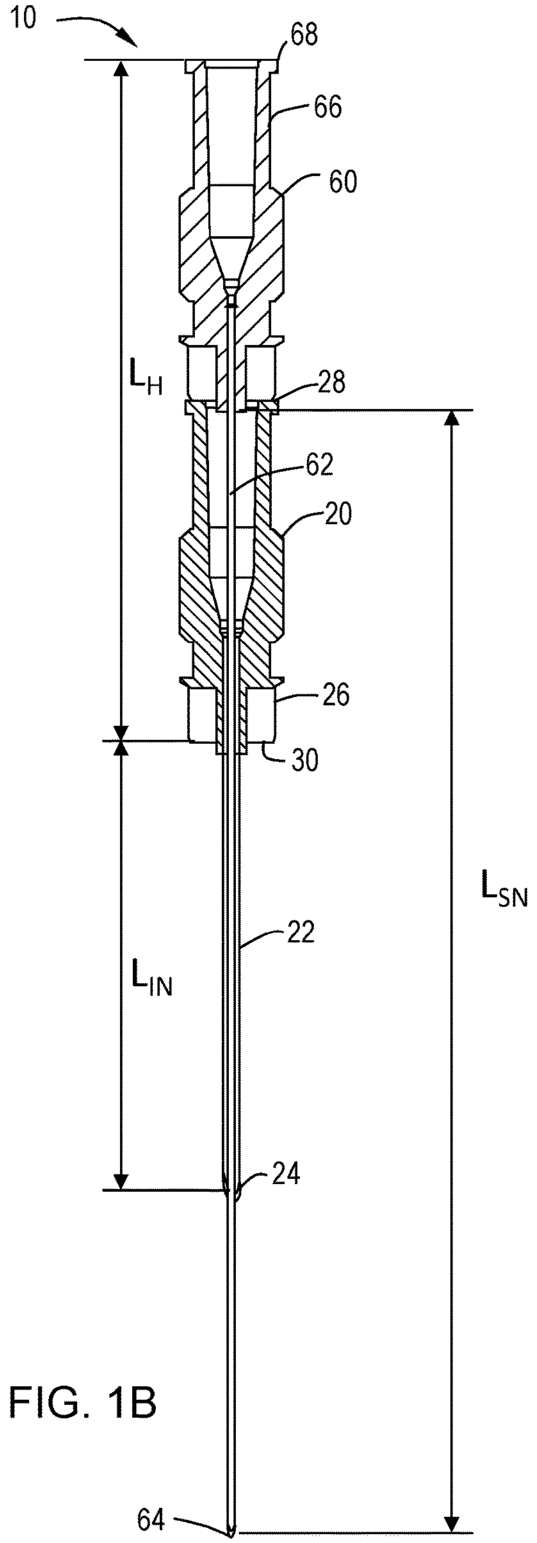
FIG. 1B illustrates a cross-sectional view of a spinal-introducer needle assembly in accordance with one or more embodiments of the present disclosure.

FIGS. 1A and 1B show an exemplary spinal-introducer needle assembly 10 comprising an introducer needle 20 and a spinal needle 60. FIG. 1A illustrates a side view of the spinal-introducer needle assembly 10 and FIG. 1B illustrates a cross-sectional view of the spinal-introducer needle assembly 10. The introducer needle 20 comprises an introducer needle cannula 22 having a distal end 24, the introducer needle cannula 22 extending from a distal end 30 of an introducer needle hub 26. The needle hub 26 comprises a proximal end 28 and the distal end 30. The spinal needle 60 comprises a spinal needle cannula 62 having a distal end 64, the spinal needle cannula 62 extending from a distal end 70 of a spinal needle hub 66. The spinal needle hub 66 comprises a proximal end 68 and the distal end 70. In the embodiments described herein, the foldable needle cover 100 of FIGS. 1 through 6D and the safety needle assembly 200 of FIGS. 7 through 12 are configured to operate with the entire spinal-introducer needle assembly 10, however in some embodiments, the foldable needle cover 100 and the safety needle assembly 200 can also be operable with only one of the introducer needle 20 or spinal needle 60. In even further embodiments, the foldable needle cover 100 and the safety needle assembly 200 is operable with conventional needles and cannulas. As the drawings are not to scale, the foldable needle cover 100 and the safety needle assembly 200 can be sized and configured to cover or protect conventional needles and cannulas of any size or gauge.

The introducer needle cannula 22 has a length $L_{IN}$ defined by the distal end 24 of introducer needle cannula 22 to the distal end 30 of introducer needle hub 26, and likewise the spinal needle cannula 62 has a length $L_{SN}$ defined by distal end 64 of spinal needle cannula 62 to the distal end 70 of spinal needle hub 66. The introducer needle cannula 22 has a needle gauge greater than a needle gauge of the spinal needle cannula 62 such that the spinal needle cannula 62 can be inserted through the introducer needle cannula 22. As shown in the figures, the introducer needle 20 receives the spinal needle 60 such that the distal end 70 of spinal needle hub 66 fully abuts the proximal end 28 of introducer needle hub 26. In such a configuration, the spinal-introducer needle assembly 10 has a total length $L_{SI}$ defined by the proximal end 68 of spinal needle hub 66 to the distal end 64 of spinal needle cannula 62. Furthermore, with the introducer needle hub 26 abutted against the, the two needle hubs (26, 66) have a total length $L_H$ defined by the proximal end 68 of spinal needle hub 66 to the distal end 30 of introducer needle hub 26. The length $L_{SN}$ of the spinal needle cannula 62 is longer than the introducer needle hub 26 and the length $L_{IN}$ of the introducer needle cannula 22 such that the distal end 64 of spinal needle cannula 62 extends beyond the distal end 24 of introducer needle cannula 22.

In some embodiments, the distal end 70 of spinal needle hub 66 abuts the proximal end 28 of introducer needle hub 26. In some embodiments, the distal end 70 of spinal needle hub 66 is at least partially inserted within the proximal end 28 of introducer needle hub 26. In some embodiments, the distal end 70 of spinal needle hub 66 is releasably secured to the proximal end 28 of introducer needle hub 26 by way of a luer connector, a snap connection or an interference fit.

In operation, the introducer needle 20 can first be inserted into the skin of a patient and the spinal needle 60 can then be inserted into the proximal end 28 of introducer needle hub 26 of the introducer needle 20. After completion of the medical procedure, the entire spinal-introducer needle assembly 10 is withdrawn together.

Figure 2:
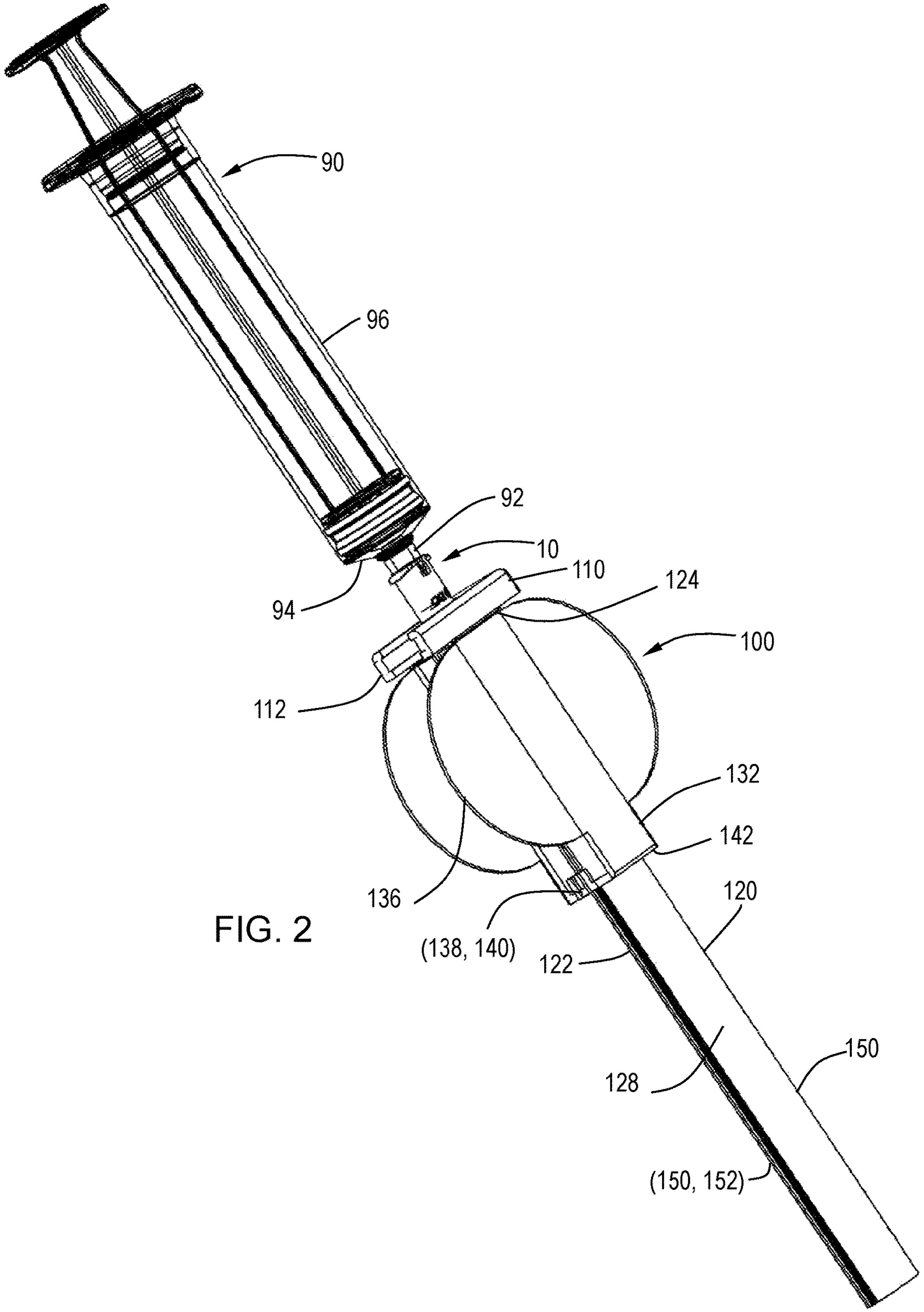
FIG. 2 illustrates a perspective view of a foldable needle cover in a closed state attached to a spinal-introducer needle assembly in accordance with one or more embodiments of the present disclosure.

FIG. 2 illustrates a syringe assembly 90 attached to the spinal-introducer needle assembly 10 by way of a luer slip connection between the proximal end 68 of spinal needle hub 66 and a luer connector 92 extending from a distal end 94 of a barrel 96 of the syringe assembly 90. In some embodiments, the syringe assembly 90 is attached to the spinal-introducer needle assembly 10 by way of a threaded connection or a snap connection.

Figure 3:
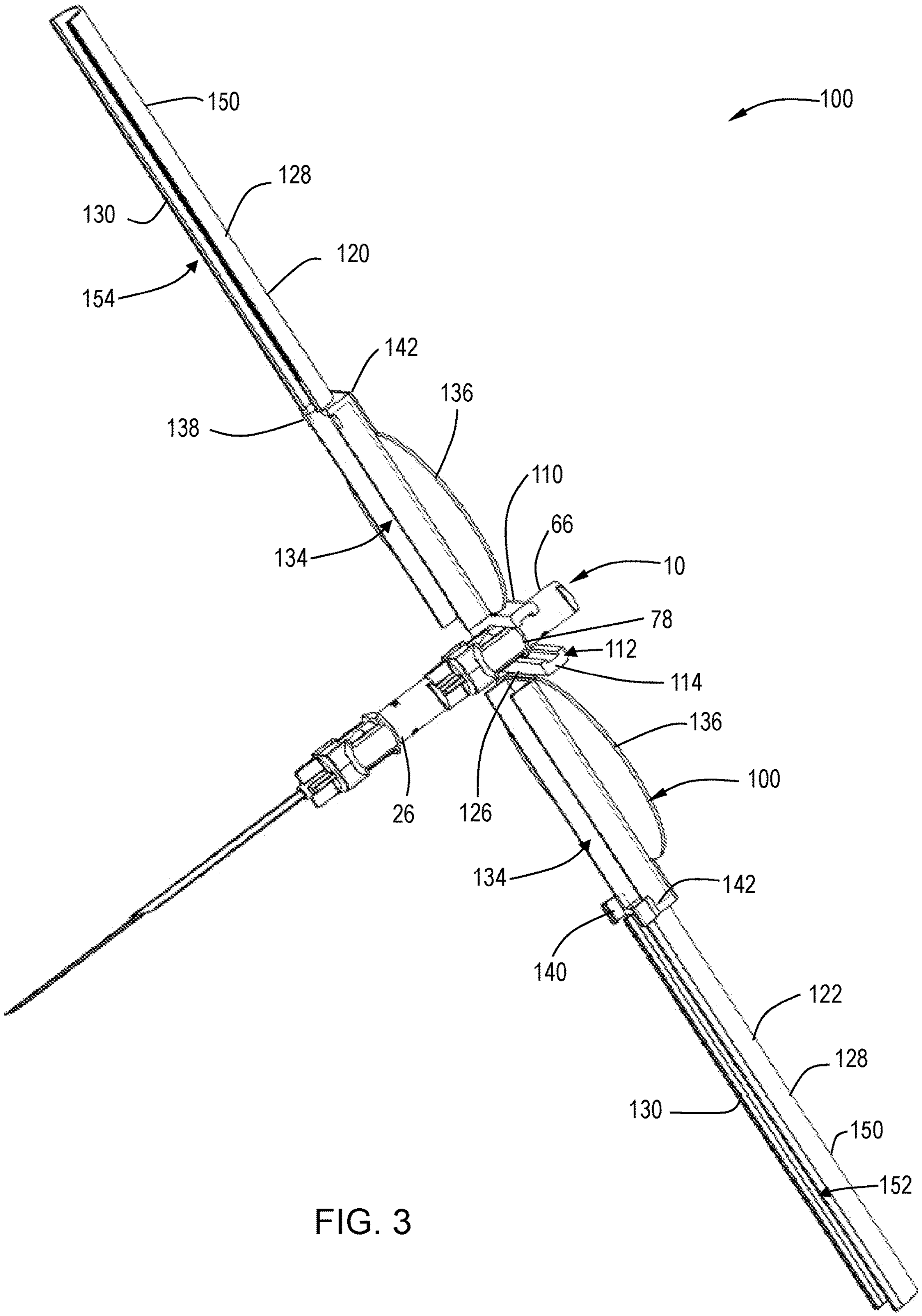
FIG. 3 illustrates a perspective view of a foldable needle cover in an open state attached to a spinal-introducer needle assembly in accordance with one or more embodiments of the present disclosure.
Figure 4:
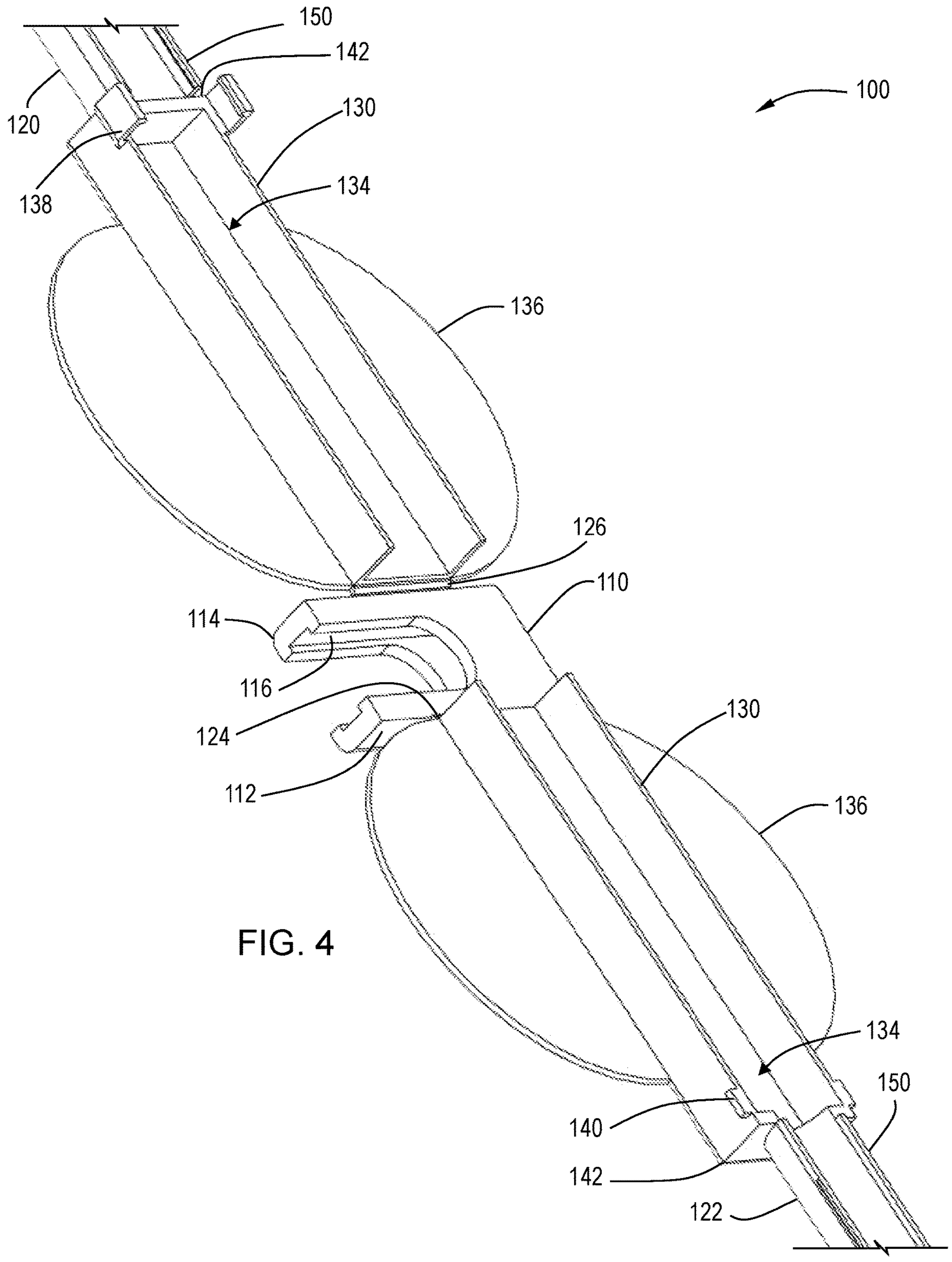
FIG. 4 illustrates a perspective view of a foldable needle cover in an open state in accordance with one or more embodiments of the present disclosure.

A foldable needle cover 100 according to one or more embodiments is removably attached to the spinal needle hub 66 as explained in further detail below. FIG. 2 illustrates the foldable needle cover 100 in a closed position and FIG. 3 illustrates the spinal-introducer needle assembly 10 attached to the foldable needle cover 100 in an open position. FIG. 4 illustrates a detailed view of the foldable needle cover 100 and FIGS. 5A and 5B illustrate cross-sectional views of the foldable needle cover 100 in the closed position with the spinal-introducer needle assembly 10 closed within.

Figure 5A:
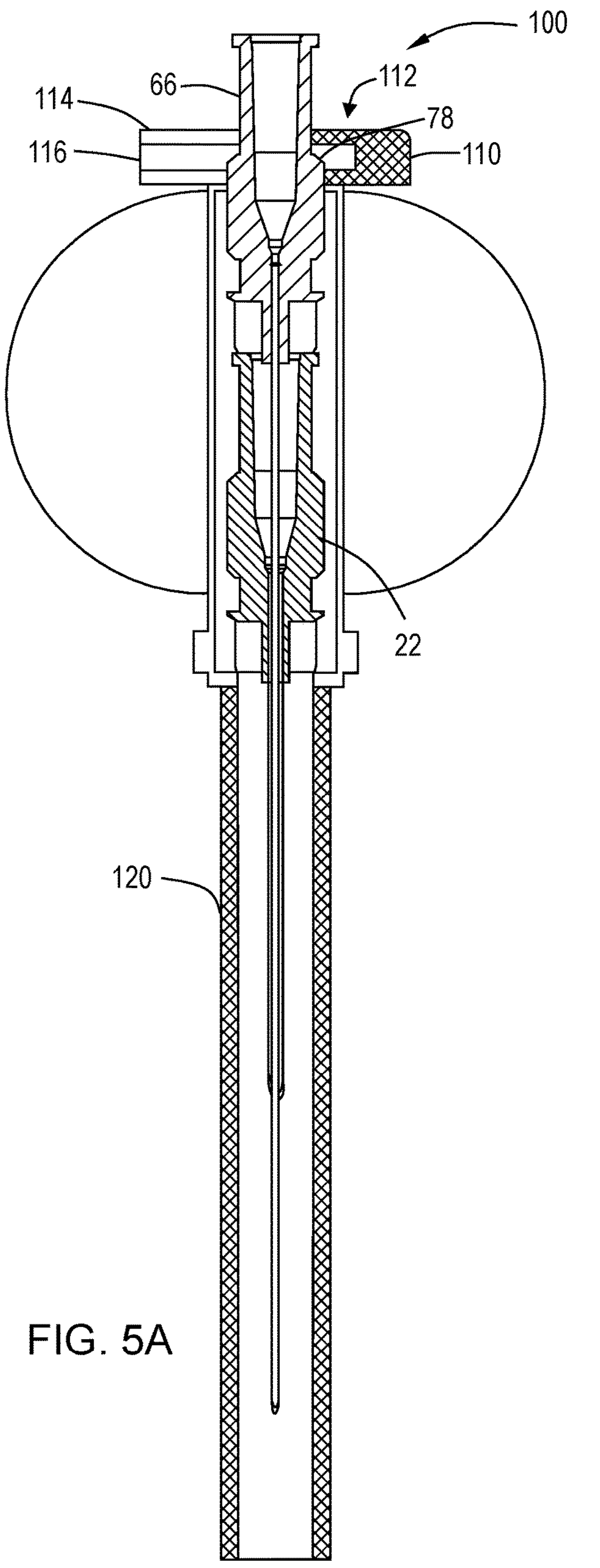
FIG. 5A illustrates a cross-sectional front view of a foldable needle cover in a closed state in accordance with one or more embodiments of the present disclosure.
Figure 5B:
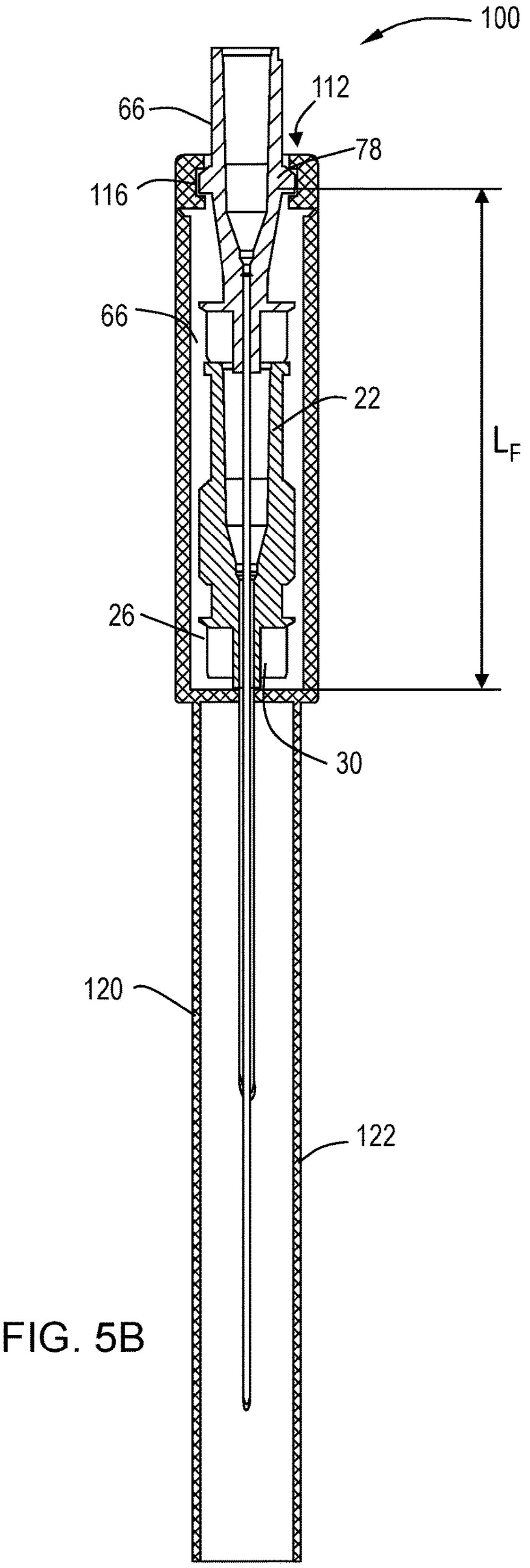
FIG. 5B illustrates a cross-sectional side view of a foldable needle cover in a closed state in accordance with one or more embodiments of the present disclosure.

As shown in FIGS. 2-4, 5A and 5B, the foldable needle cover comprises a rectangular base 110 which removably attaches to the spinal-introducer needle assembly 10 via a connecting feature 112. In the embodiments depicted, the connecting feature 112 is in the form of a pair of teeth 114 which interdigitate with a flange 78 of the spinal needle hub 66 as best shown in FIGS. 5A and 5B. The pair of teeth 114 form a channel 116 between them in which the flange 78 of the spinal needle hub 66 slides into. As best shown in FIGS. 5A and 5B, in some embodiments, the pair of teeth 114 have a u-shaped cross-section which can be sized and dimensioned to accommodate the flange 78 of the spinal needle hub 66. In some embodiments, the width between the pair of teeth 114 is configured to create an interference fit between the flange 78 of the spinal needle hub 66 and the pair of teeth 114. In some embodiments, the u-shaped cross-section is configured to prevent longitudinal movement of the connecting feature 112.

In some embodiments, the pair of teeth 114 and channel 116 are configured to interdigitate with a feature of the introducer needle hub 26. In some embodiments, the pair of teeth 114 and channel 116 are configured to interdigitate with ridges, flanges or valleys of the introducer needle hub 26 and the spinal needle hub 66. In some embodiments, the pair of teeth 114 and channel 116 are configured create an interference fit with the feature it removably attaches to.

The foldable needle cover 100 further comprises a two-piece hinged cap (120, 122) connected to the base 110 by two living hinges (124. 126), each living hinge of the two living hinges (124. 126) corresponding to a hinged cap of the two-piece hinged cap (120, 122). Each two-piece hinged cap (120, 122) is configured to pivot at least 180 degrees around each of the two living hinges (124. 126) from an open position as shown in FIG. 3 to a closed position as shown in FIG. 2.

The foldable needle cover 100, base 110 and two-piece hinged cap (120, 122) have a proximal surface 128 and a distal surface 130 in the open position as shown in FIG. 3. For purposes of clarity, said surfaces shall still be referred to as proximal and distal even when the foldable needle cover 100 is in the closed position as shown in FIG. 2.

As shown in the FIG. 3, the two-piece hinged cap (120, 122) is initially in an open position with the distal surface 130 of each two-piece hinged cap (120, 122) facing in a distal direction. As shown in FIG. 2, in the closed position the distal surface 130 of each two-piece hinged cap (120, 122) has rotated 90 degrees relative to the depicted initial position, closing each distal surface 130 of each two-piece hinged cap (120, 122) onto the other, thereby enclosing the spinal-introducer needle assembly 10 within.

Each of the two-piece hinged cap (120, 122) has a medial portion 132 and a lateral portion 150 relative to the base 110. The medial portion 132 of some embodiments is rectangular in shape and has a rectangular cavity 134 formed on the distal surface 130. As shown in FIGS. 5A and 5B, the medial portion 132 is configured to cover and accommodate the assembled introducer needle hub 26 and spinal needle hub 66. As shown in FIG. 4, the rectangular shape of the medial portion 132 of both of the two-piece hinged cap (120, 122) is connected to the rectangular base 110 by the living hinge (124, 126), the living hinge (124, 126) extending the entire width of the rectangular shape of the medial portion 132, thereby providing greater support for the living hinge (124, 126).

As shown in FIG. 5B, the rectangular cavity 134 has a length $L_F$ extending from the flange 78 of the spinal needle hub 66 (onto which the connecting feature 112 of the foldable needle cover 100 attaches to) slightly past the distal end 30 of the introducer needle hub 26 such that the introducer needle hub 26 and spinal needle hub 66 are fully enclosed within the rectangular cavity 134. “Slightly past” within the context of the length $L_F$ is a length $L_F$ which has sufficient clearance to accommodate the distal end 30 of the introducer needle hub 26.

In some embodiments, the rectangular cavity 134 is configured to also cover and accommodate the entire length $L_{SN}$ of the spinal needle 60, thereby completely covering the entire spinal-introducer needle assembly 10 from the flange 78 of the spinal needle hub 66 to the spinal needle 60. In some embodiments, the medial portion 132 of each two-piece hinged cap (120, 122) further includes a winged tab 136 extending from the proximal surface 128. The winged tab 136 configured to provide a greater surface area for manipulating and closing the two-piece hinged cap (120, 122).

In some embodiments, the foldable needle cover 100 disclosed herein is configured to interdigitate, slide onto or otherwise removably attach to one or more features of either of the introducer needle hub 26 or the spinal needle hub 66. Such features can include ridges, flanges or valleys of either of the introducer needle hub 26 or the spinal needle hub 66. In some embodiments, ridges can include a ridge 32 of introducer needle hub 26 or a ridge 72 of spinal needle hub 66 as shown in FIGS. 1A and 1B. Flanges can include a flange 34 of introducer needle hub 26 or a flange (74, 78) of spinal needle hub 66 as shown in FIGS. 1A, 1B, 5A and 5B. Valleys can include a valley 76 of spinal needle hub 66 or a valley 76 of spinal needle hub 66 as shown in FIGS. 1A and 1B. Thus, where FIG. 5B illustrates the length $L_F$ of the rectangular cavity 134 extending from the flange 78 of the spinal needle hub 66 (onto which the connecting feature 112 of the foldable needle cover 100 attaches to) slightly past the distal end 30, the connecting feature 112 of the foldable needle cover 100 can interdigitate with a different feature, thereby changing the length of the rectangular cavity 134. By way of example, but not limitation, in some embodiments, the connecting feature 112 of the foldable needle cover 100 can connect to the flange 74 of the spinal needle hub 66 as shown in FIG. 1A. In such a configuration, the length of the rectangular cavity 134 can be less than the length $L_F$ due to the connecting feature 112 being configured to connect to a different feature or element of the spinal-introducer needle assembly 10.

In some embodiments, the medial portion 132 of each of the two-piece hinged cap (120, 122) as shown in FIGS. 2-4, further includes snap locks (138, 140) which are configured to lock with one another upon closure of the two-piece hinged cap (120, 122). In some embodiments, the snap locks (138, 140) are configured to non-removably lock with one another upon closure of the two-piece hinged cap (120, 122). In some embodiments, one of the snap locks 140 is configured as a set of tabs projecting from the medial portion 132 and the other of the snap locks 138 is configured as a set of hooks which can elastically deform and engage with the set of tabs. In some embodiments, the snap locks (138, 140) are located at a lateral end 142 of the medial portion 132.

Adjacent and lateral to the lateral end 142 of the medial portion 132, a lateral portion 150 extends therefrom. The lateral portion 150 is configured to envelop the introducer needle cannula 22 and the introducer needle hub 26. In some embodiments, distal edges (152, 154) of the lateral portion

150 of each of the two-piece hinged cap (120, 122) are configured to interlock with one another in a snap-fit configuration. In some embodiments, edges (152, 154) of the lateral portion 150 of each of the two-piece hinged cap (120, 122) are configured to non-removably interlock with one another in a snap-fit configuration.

Due to the live-hinge configuration of the foldable needle cover 100, the foldable needle cover 100 can be injection molded forming a singular unitary body. Thus, the foldable needle cover 100 can be cheap to manufacture from a single mold and can be included in a kit for an anesthesia needle assembly. Furthermore, as explained in further detail below, the foldable needle cover 100, (due to its connecting feature 112 being slidable onto a hub of the spinal-introducer needle assembly 10) can be attached to the spinal-introducer needle assembly 10 while the spinal-introducer needle assembly 10 is still inserted within the skin of a patient. Thus, in operation, a practitioner can attach the foldable needle cover 100 onto the spinal-introducer needle assembly 10, and upon removal of the spinal-introducer needle assembly 10, the foldable needle cover 100 can be non-removably closed together as the spinal-introducer needle assembly 10 is removed from the skin of a patient. Thus, the step of re-inserting the introducer needle hub 26 or the spinal needle hub 66 back into a needle-sleeve is not required as the foldable needle cover 100 fully envelops the entire spinal-introducer needle assembly 10.

Figure 6A:
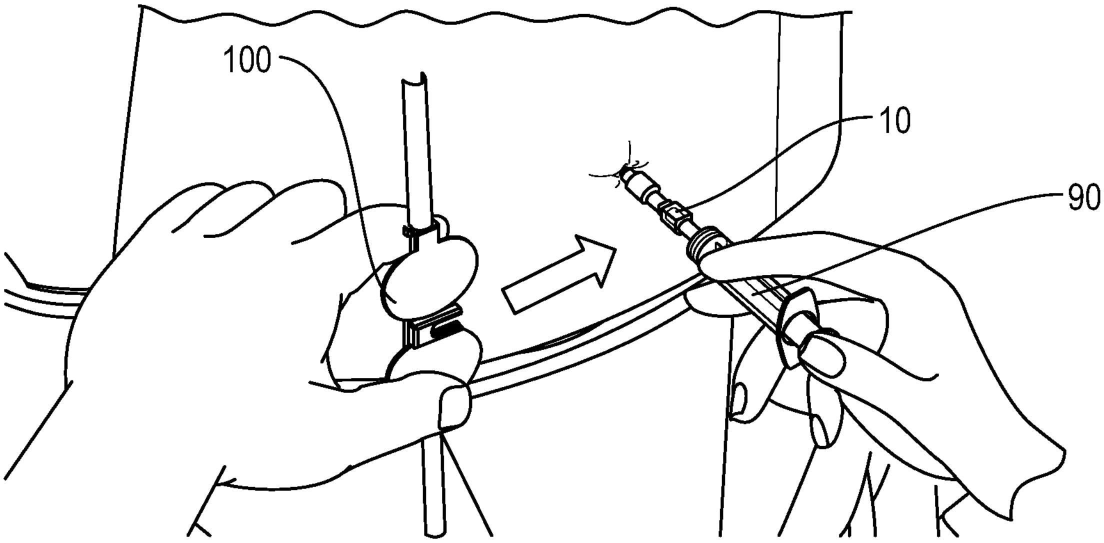
FIGS. 6A through 6D illustrate a method of covering a spinal-introducer needle assembly in accordance with one or more embodiments of the present disclosure.
Figure 6B:
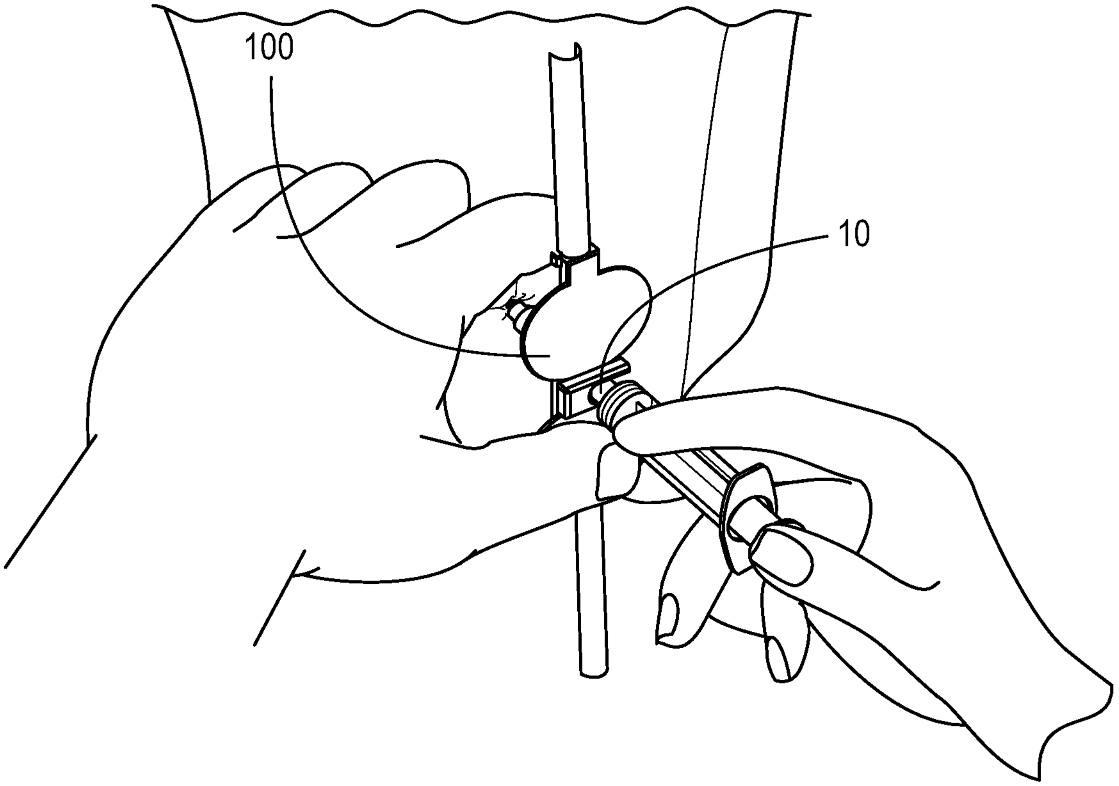
Figure 6C:
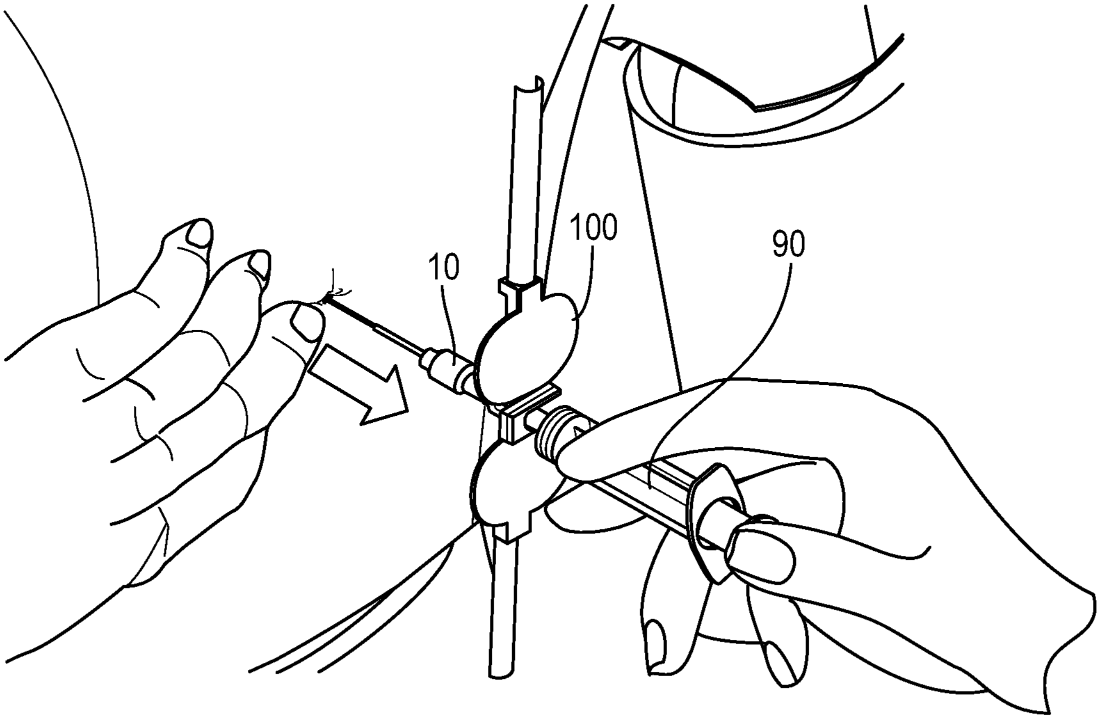
Figure 6D:
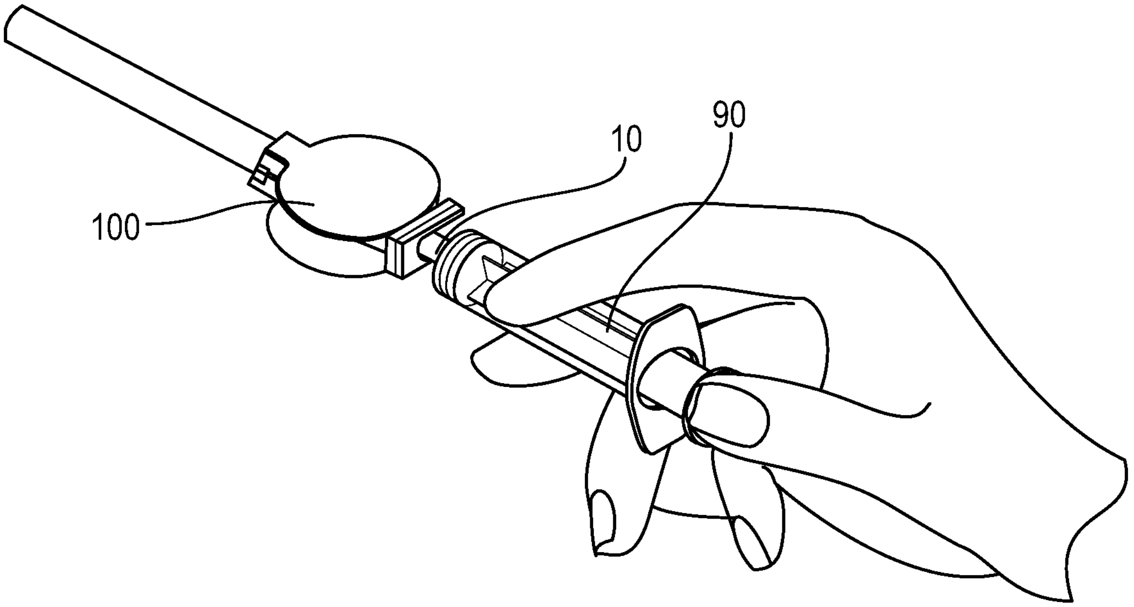

FIGS. 6A through 6D illustrate a method of covering a spinal-introducer needle assembly 10 within a foldable needle cover 100 in accordance with one or more embodiments of the present disclosure. As shown in FIG. 6A, the method includes the steps of holding the syringe assembly 90 and spinal-introducer needle assembly 10 with one hand and the foldable needle cover 100 with the other hand. As shown in FIG. 6B, the method further includes the steps of sliding the foldable needle cover 100 in a medial direction relative to the syringe assembly 90 over the spinal-introducer needle assembly 10 as previously described. In some embodiments, the foldable needle cover 100 is slidable over the spinal-introducer needle assembly 10 while the spinal-introducer needle assembly 10 is still at least partially inserted within the skin of a patient. As shown in FIG. 6C, the method further includes the step of withdrawing the spinal-introducer needle assembly 10 and syringe assembly 90 with one hand from the skin of a patient while the foldable needle cover 100 is still attached to the spinal-introducer needle assembly 10. As shown in FIG. 6D, the method further includes the step of closing the foldable needle cover 100 over the spinal-introducer needle assembly 10 by depressing the winged tabs 136, thereby causing the two-piece hinged cap (120, 122) to pivot on the two living hinges (124. 126). In some embodiments, the steps of FIGS. 6C and 6D can be completed simultaneously, where a practitioner performs the steps of withdrawing the spinal-introducer needle assembly 10 while simultaneously closing the foldable needle cover 100 over the spinal-introducer needle assembly 10 by depressing the winged tabs 136. In some embodiments, the closed foldable needle cover 100 in the closed position along with the spinal-introducer needle assembly 10 can be safely disposed of.

As shown in FIGS. 7-12, embodiments of the present disclosure are further directed to a safety needle assembly 200 comprising the introducer needle 20 as previously described, a two-piece hinged cap (220, 222) and a sliding block 260 configured to open or close the two-piece hinged cap (220, 222). In some embodiments, the safety needle assembly 200 further comprises the spinal needle 60 connected to the introducer needle 20 as previously described. The sliding block 260 is configured to open or close the two-piece hinged cap (220, 222) as the sliding block 260 is translated from a proximal to distal direction without having to further manipulate the safety needle assembly 200 or the two-piece hinged cap (220, 222) as explained in further detail below.

Figure 7:
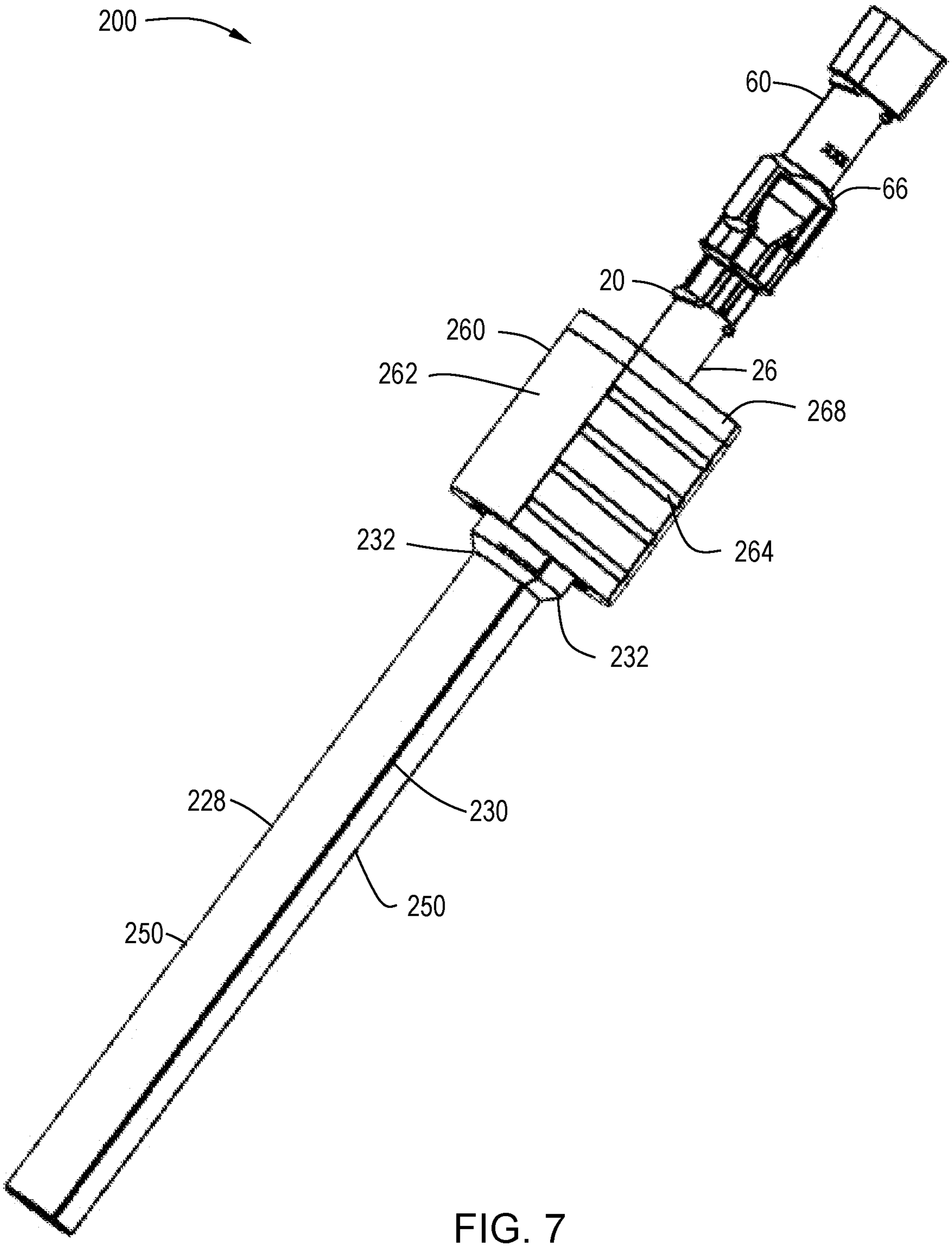
FIG. 7 illustrates a perspective view of the safety needle assembly in a closed position in a closed state in accordance with one or more embodiments of the present disclosure.
Figure 8:
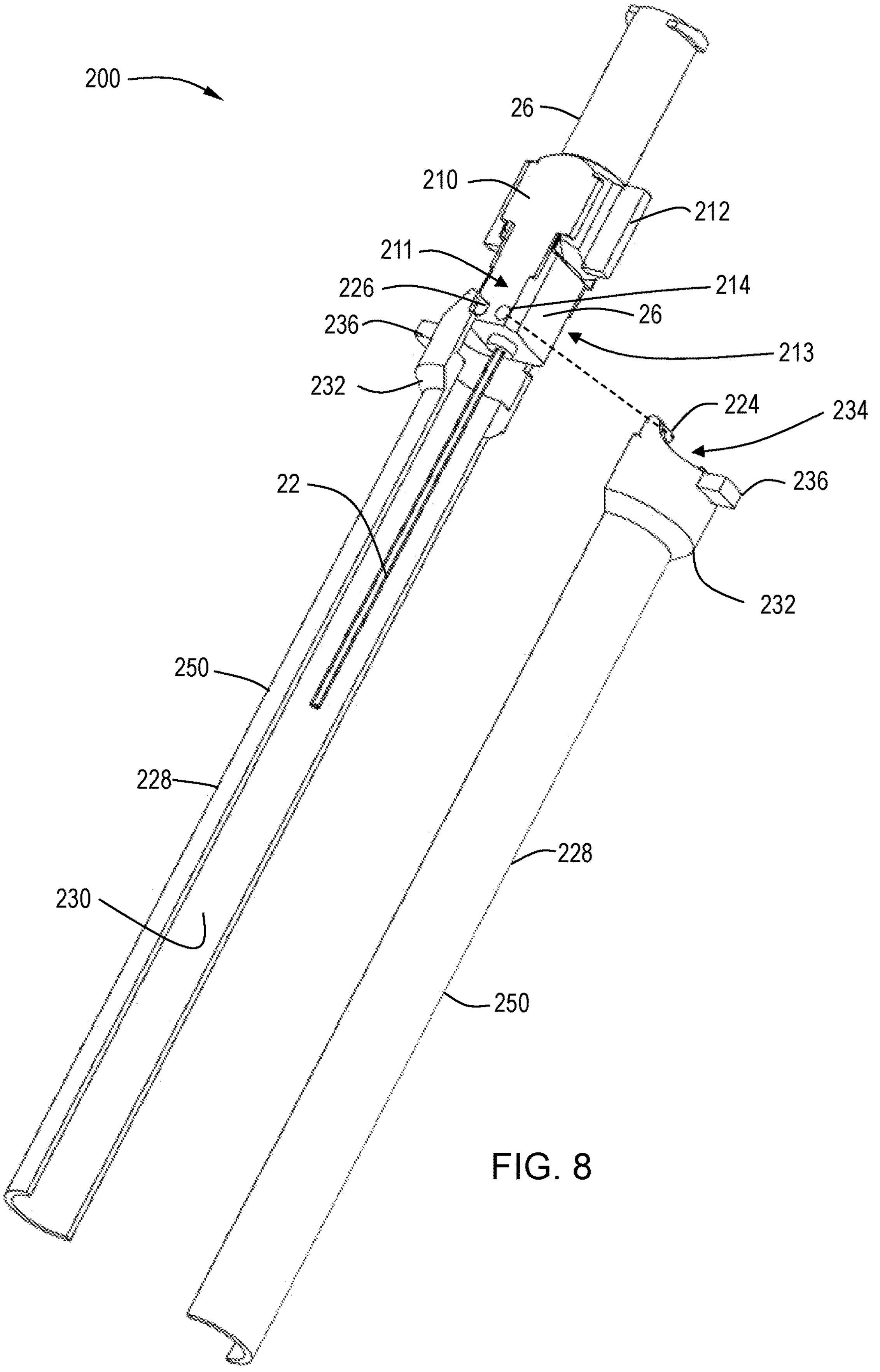
FIG. 8 illustrates a perspective view of the safety needle assembly with one of the two-piece hinged cap separated from the safety needle assembly in accordance with one or more embodiments of the present disclosure.
Figures 9, 10:
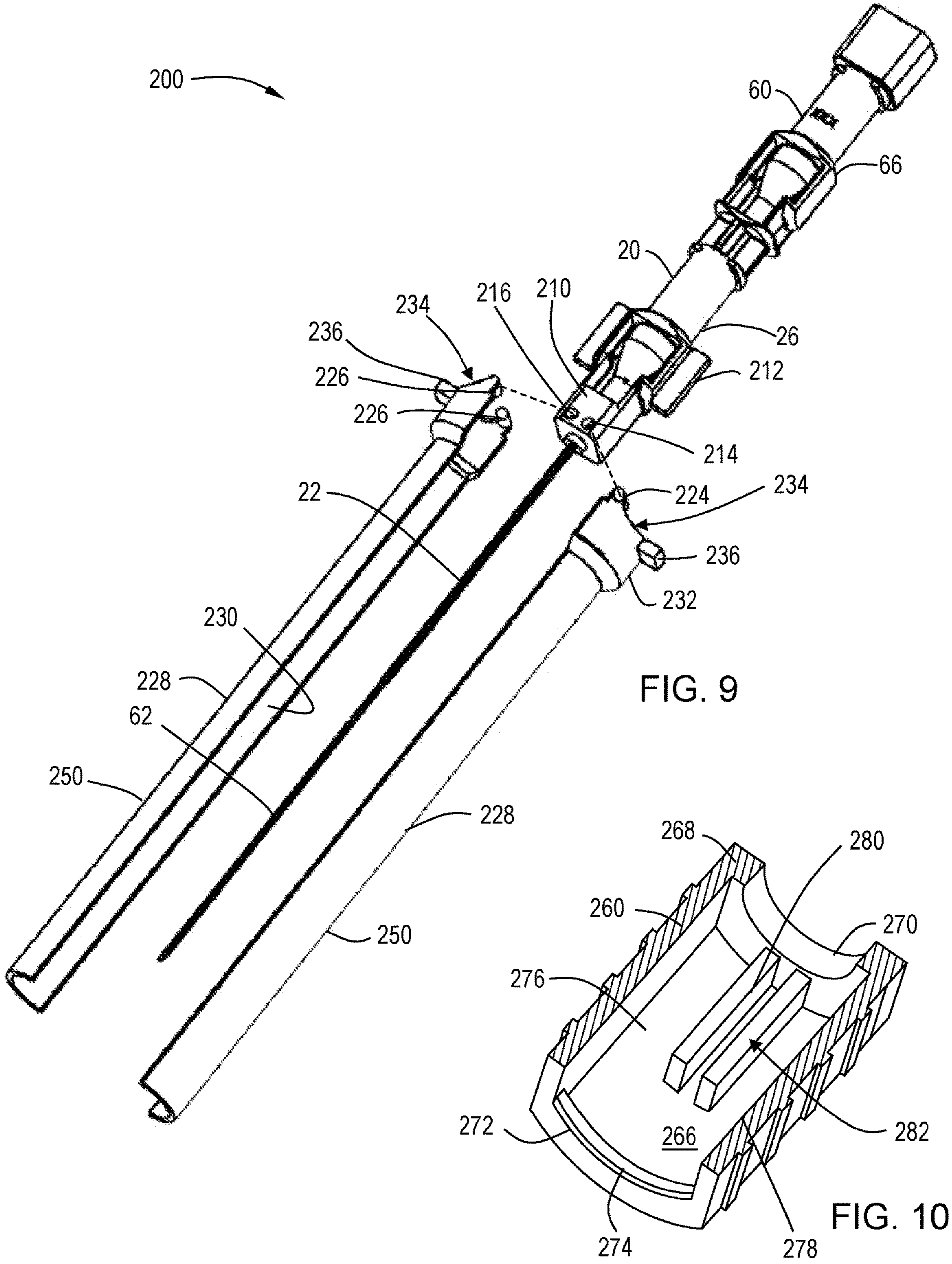
FIG. 9 illustrates the illustrates a perspective view of the safety needle assembly with both of the two-piece hinged cap separated from the safety needle assembly in accordance with one or more embodiments of the present disclosure.
FIG. 10 illustrates a cross-sectional view of a sliding block in accordance with one or more embodiments of the present disclosure.
Figure 11A:
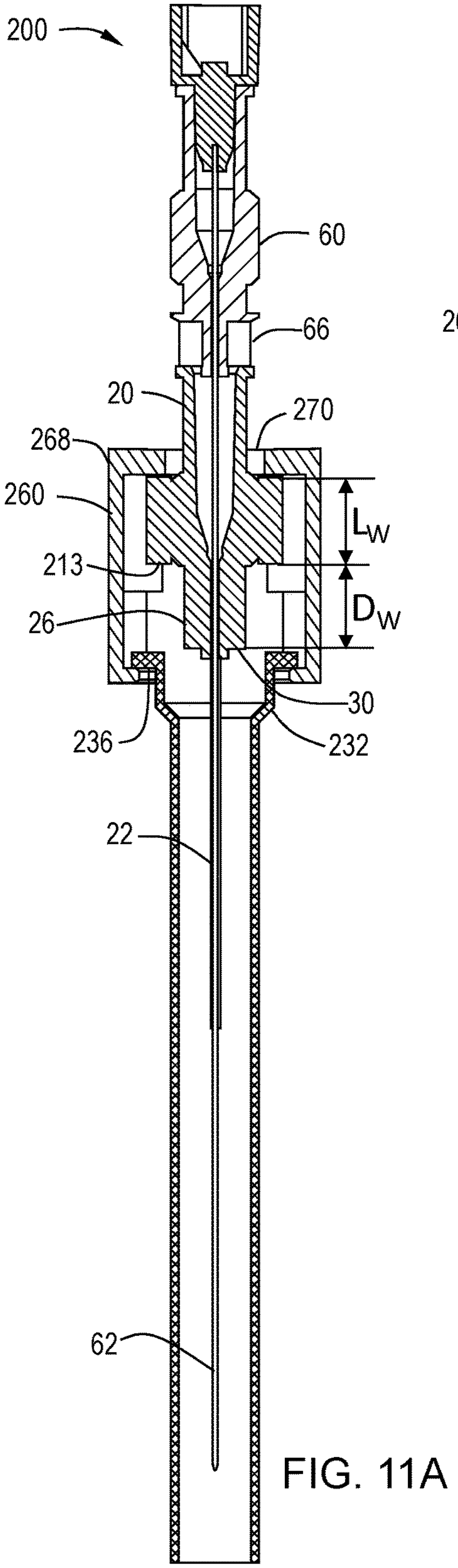
FIG. 11A illustrates a cross-sectional view of the safety needle assembly in accordance with one or more embodiments of the present disclosure.
Figure 11B:
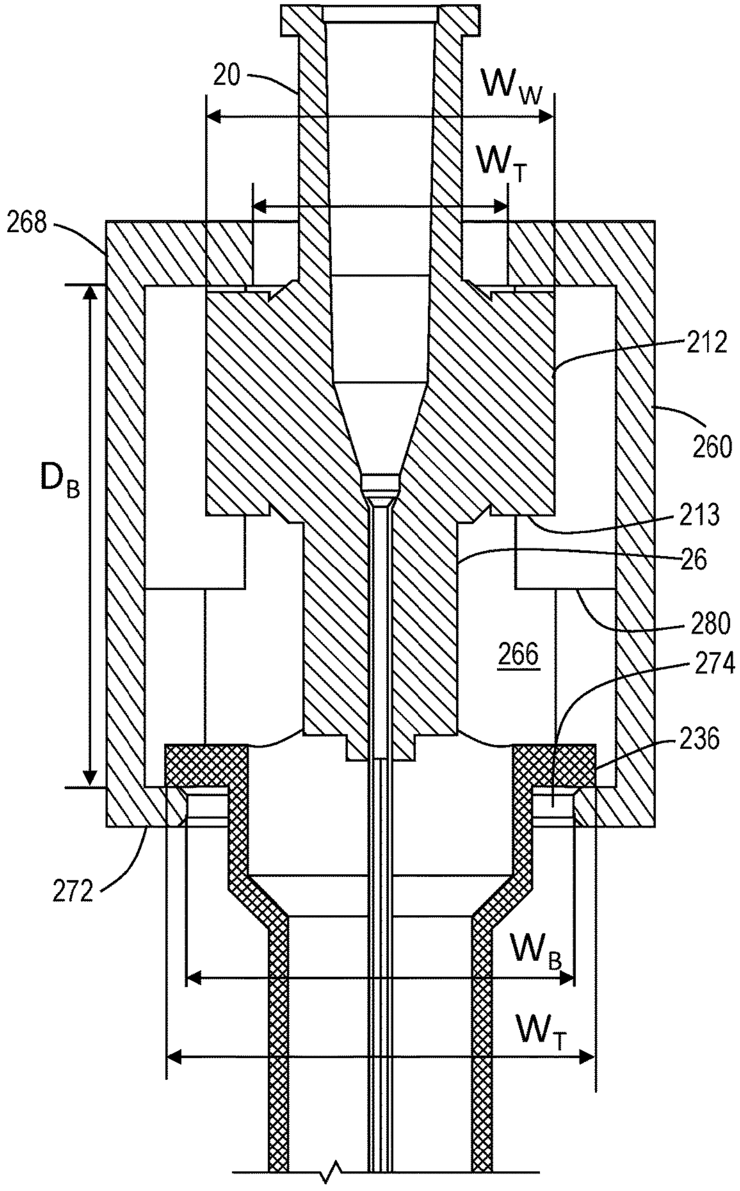
FIG. 11B illustrates a detailed cross-sectional view of the safety needle assembly in accordance with one or more embodiments of the present disclosure; and, FIG. 12 illustrates a cross-sectional view of the safety needle assembly in an open position in accordance with one or more embodiments of the present disclosure.
Figure 12:
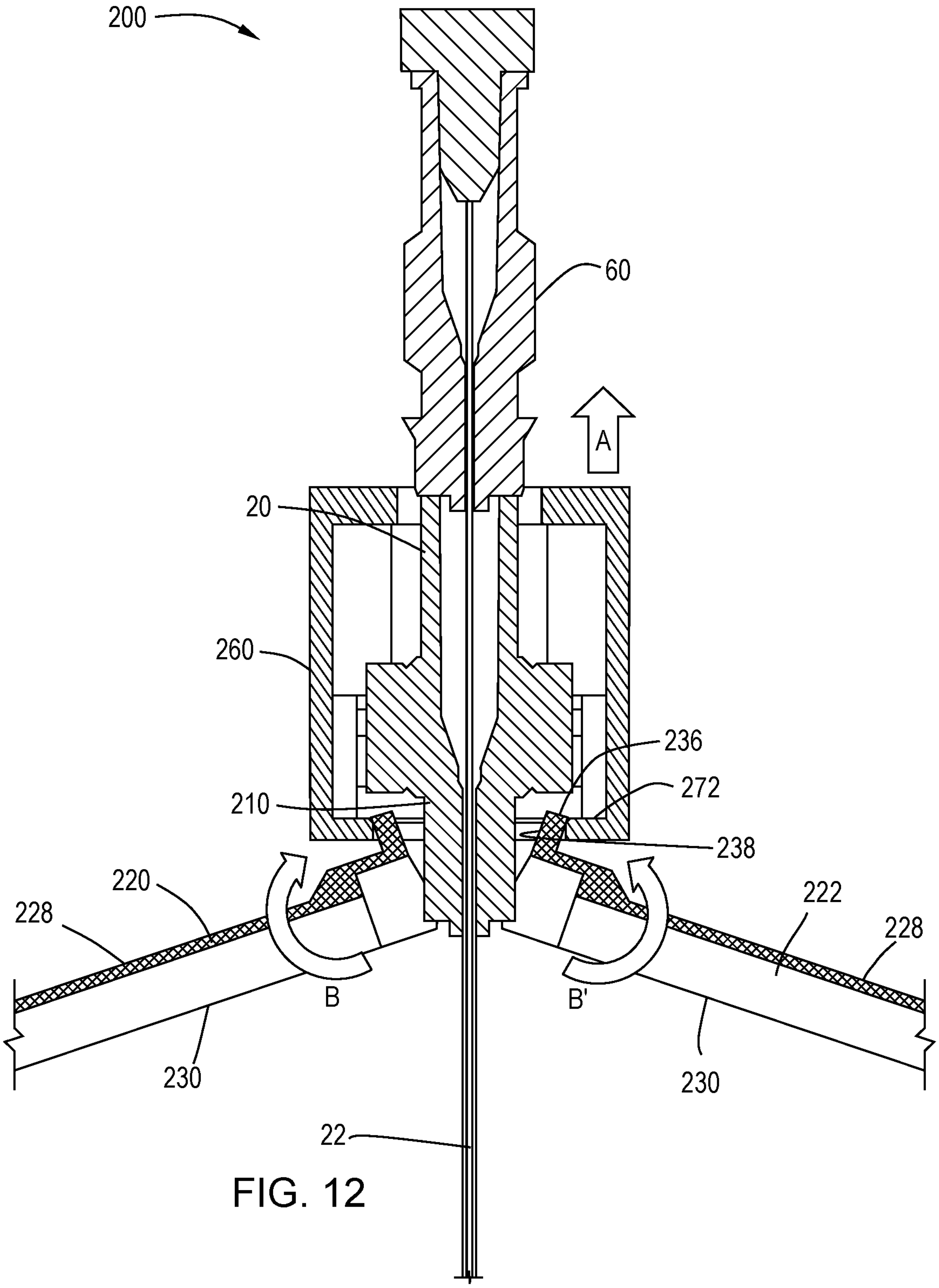

FIG. 7 illustrates a perspective view of the safety needle assembly 200 in a closed position. FIG. 8 illustrates a perspective view of the safety needle assembly 200 with one of the two-piece hinged cap (220, 222) separated from the safety needle assembly 200. FIG. 9 illustrates the illustrates a perspective view of the safety needle assembly 200 with both of the two-piece hinged cap (220, 222) separated from the safety needle assembly 200. FIG. 10 illustrates a cross-sectional view of the sliding block 260. FIG. 11A illustrates a cross-sectional view of the safety needle assembly 200 and FIG. 11B illustrates a detailed cross-sectional view of the safety needle assembly 200. FIG. 12 illustrates a cross-sectional view of the safety needle assembly 200 in an open position.

As shown in FIGS. 7 through 9, the introducer needle 20 further includes a pair of wings 212 extending longitudinally from an outside surface 210 of the introducer needle hub 26. The introducer needle 20 further includes attachment points (214, 216) on the outside surface 210 of the introducer needle hub 26 for connecting the two-piece hinged cap (220, 222) to the introducer needle hub 26 as explained in further detail below. In some embodiments, the introducer needle hub 26 is a rectangular elongated body. In some embodiments, the introducer needle hub 26 is a circular or oval elongated body. In some embodiments, the introducer needle hub 26 is a rectangular elongated body with opposing flat faces. In some embodiments, as shown in FIG. 8, the attachment points (214, 216) are located on opposing flat faces 211 of the introducer needle hub 26.

The attachment points (214, 216) in the depicted embodiments consist of two pairs of apertures partially extending into the outside surface 210 of introducer needle hub 26 and are located on opposite sides on the introducer needle hub 26. Each of the two pairs of apertures and the attachment points (214, 216) are configured to create a snap connection with a pair of corresponding attachment points (224, 226) of the two-piece hinged cap (220, 222). In some embodiments, the attachment points (214, 216) of the introducer needle hub 26 are positioned at a right angle relative to the pair of wings 212 of the introducer needle hub 26. Stated differently and as best shown in FIG. 8, in some embodiments the attachment points (214, 216) are located on opposing flat faces 211 of the introducer needle hub 26 and the pair of wings 212 extend from faces 213 which is at a right angle with the opposing flat faces 211 of the attachment points (214, 216). In some embodiments, the faces 213 are also flat.

In some embodiments, the attachment points (214, 216) of the introducer needle hub 26 are positioned at the distal end 30 of the introducer needle hub 26. In some embodiments, as shown in FIG. 11A, a distal edge 213 the pair of wings 212 is positioned a distance $D_W$ from the distal end 30 of introducer needle hub 26, and the pair of wings 212 have a longitudinal length $L_W$. Furthermore, as shown in FIG. 11B, the pair of wings 212 have a total width $W_W$ defined by the distance between the pair of wings 212.

Referring back to FIGS. 7 through 9, each of the two-piece hinged cap (220, 222) has a proximal surface 228 and a distal surface 230, the distal surfaces of the two-piece hinged cap (220, 222) configured to close on each other. The two-piece hinged cap (220, 222) has an elongated body with a cavity within the distal surface 230. As shown in FIG. 12, the two-piece hinged cap (220, 222) is initially in an open position with the distal surface 230 of each two-piece hinged cap (220, 222) are facing in a distal direction. As shown in FIG. 7, in the closed position the distal surface 230 of each two-piece hinged cap (220, 222) has closed relative to the depicted initial position, thereby closing each distal surface 230 of each two-piece hinged cap (220, 222) onto the other and enclosing the introducer needle cannula 22 and spinal needle cannula 62 within.

Each of the two-piece hinged cap (220, 222) has a medial portion 232 and a lateral portion 250. Each of the medial portion 232 comprises a tab 236 extending from the proximal surface 228 in a proximal direction relative to the proximal surface 228 and the pair of corresponding attachment points (224, 226). In the depicted embodiments, the pair of corresponding attachment points (224, 226) are in the form of tabs or protrusions positioned on the distal surface 230 and extend inwardly such that the tabs or protrusions are opposite each other. The tabs or protrusions are configured to interrogate in a snap-lock configuration with the apertures of the attachment points (214, 216) of the introducer needle hub 26.

As used herein, the term "attachment points (214, 216) of the introducer needle hub 26" refer to a pair of attachment points (214, 216) positioned on opposing faces of the introducer needle hub 26 as previously described. Thus, a first pair of attachment points 214 comprises two apertures on opposing faces 213 of the of the introducer needle hub 26 and a second pair of attachment points 216 adjacent to the first pair of attachment points 214. Thus, the introducer needle hub 26 has a total of four apertures which each interdigitate with the corresponding attachment points (224, 226). In the figures, only two apertures are shown, however it is to be understood that the two unshown apertures are positioned opposite the face presented in the figures. Likewise, as used herein the term "pair of corresponding attachment points (224, 226)" refer to two tabs or protrusions for each of the two-piece hinged cap (220, 222). Thus, a first pair of the corresponding attachment points 224 interdigitates with the first pair of attachment points 214 of the introducer needle hub 26 and a second pair of the corresponding attachment points 226 interdigitates with the first pair of attachment points 216. The tabs and apertures described form snap-fit configurations in which a tab is seated within an aperture by elastically deforming the two-piece hinged cap (220, 222) over the introducer needle hub 26.

As shown in FIG. 8, the tab 236 extends in a perpendicular plane relative to the pair of corresponding attachment points (224, 226) of the two-piece hinged cap (220, 222). As shown in FIGS. 8 and 11B where the two-piece hinged cap (220, 222) is in the closed position, the tabs 236 of the two-piece hinged cap (220, 222) are on the same plane as the pair of wings 212, and are on a perpendicular plane to the attachment points (214, 216) of the introducer needle hub 26 and the corresponding attachment points (224, 226) of the two-piece hinged cap (220, 222). As shown in FIG. 11B, the tabs 236 have a total width $W_T$ as defined by the length between proximal edges of the tabs 236. The two-piece hinged cap (220, 222) in some embodiments has a greater cross-sectional width than the lateral portion 250 and further comprises a medially-located cut-out 234 to permit a wider range of motion when opening the two-piece hinged cap (220, 222) relative to the introducer needle hub 26. As shown in FIGS. 5A and 5B, the lateral portion 250 is configured to cover and accommodate the introducer needle cannula 22 and the spinal needle cannula 62.

As shown in FIGS. 7 and 10-12, the safety needle assembly 200 further comprises a sliding block 260 having an elongated body having a substantially cylindrical cross-sectional shape. In some embodiments, the sliding block 260 is rectangular in shape. In some embodiments, the sliding block 260 is oval in shape. In some embodiments, the sliding block 260 is rectangular in shape with two flat faces and two rounded faces. In some embodiments, the sliding block 260 comprises gripping features 264 at least partially covering the outside surface 262 of one or more faces of the sliding block 260. As shown in FIG. 7, in some embodiments the gripping features 264 are a plurality of ribs.

As shown in FIGS. 10 and 11A-11B, the sliding block 260 is hollow having a cavity 266, a proximal wall 268 having a proximal wall opening 270, and a distal wall 272 and a distal wall opening 274. Between the proximal wall 268 and distal wall 272 extends a side wall 276 having an inside surface 278. From the inside surface 278 of the side wall 276 a set of protrusions 280 extend in a medial direction away from the inside surface 278. The set of protrusions 280 in some embodiments also extend longitudinally from the proximal wall 268 to the distal wall 272. The set of protrusions 280 in some embodiments also extend longitudinally from the proximal wall 268 to a distance towards the distal wall 272. The set of protrusions 280 in some embodiments also extend longitudinally a distance from the proximal wall 268 to a distance towards the distal wall 272. The set of protrusions 280 define a channel 282 in which the pair of wings 212 of the introducer needle hub 26 can slide proximally or distally between the proximal wall 268 and distal wall 272 of the sliding block 260. The channel 282 is configured to limit rotational movement of the introducer needle hub 26.

In some embodiments, the proximal wall 268 is separable from the sliding block 260. In some embodiments, the proximal wall 268 is a unitary body with the sliding block 260. In some embodiments, the proximal wall 268 is removably or non-removably threaded or snap-fit onto the sliding block 260. In some embodiments, the proximal wall 268 is non-removably adhered, welded, sonic welded or otherwise non-removably attached onto the sliding block 260.

As shown in FIG. 11B, the proximal wall opening 270 has a width $W_T$ which is less than the total width $W_W$ of the pair of wings 212 but greater than the width of the introducer needle hub 26 such that the introducer needle hub 26 can slide through the proximal wall opening 270. Likewise, the distal wall distal wall opening 274 has a width $W_B$ which is less than the total width $W_T$ of the tabs 236 but greater than the width of the introducer needle hub 26 such that the introducer needle hub 26 can slide through the distal wall opening 274. In some embodiments, a distance $D_B$ defined by the proximal wall 268 to the distal wall 272 can be configured to have the proximal wall 268 abutting the pair of wings 212 and the distal wall 272 abutting the tabs 236 of the two-piece hinged cap (220, 222) in the closed position.

In such a configuration, the sliding block 260 can longitudinally travel relative to the introducer needle hub 26 in a distal direction until the pair of wings 212 abuts against the proximal wall 268, and in a proximal direction until the two-piece hinged cap (220, 222) are opened 180 degrees relative to each other as explained in further detail below.

As shown in FIG. 8, the two-piece hinged cap (220, 222) can be attached to the attachment points (214, 216) of the introducer needle hub 26 by way of the pair of corresponding attachment points (224, 226) of the two-piece hinged cap (220, 222). In such a configuration, each of the two-piece hinged cap (220, 222) can freely pivot around the attachment points (214, 216) of the introducer needle hub 26. In some embodiments, the two-piece hinged cap (220, 222) can freely pivot between 0 degrees at the closed position as shown in FIG. 7 to 90 degrees from the fully closed position to an open position. Stated differently, each of the two-piece hinged cap (220, 222) opens 90 degrees relative to the closed position, and each of the two-piece hinged cap (220, 222) are 180 degrees from each other. In some embodiments, each of the two-piece hinged cap (220, 222) can open more than 90 degrees.

As shown in FIG. 11A, after the two-piece hinged cap (220, 222) is attached to the introducer needle hub 26, the sliding block 260 can be slid onto the introducer needle hub 26. The proximal wall 268 can be slid from a proximal to distal direction and the sliding block 260 absent the proximal wall 268 can be slid from a distal to proximal direction until the proximal wall 268 and the sliding block 260 can be removably or non-removably attached to one another as previously described. Thus, the initial and fully closed position is defined by the proximal wall 268 abutting the proximal surface of the pair of wings 212 of the introducer needle hub 26 and the distal wall 272 abutting the bottom surface of the tabs 236 of the two-piece hinged cap (220, 222), and the two-piece hinged cap (220, 222) is closed.

As shown in FIG. 12, and as illustrated by the arrow indicating motion, the sliding block 260 is pulled by one hand in a proximal direction as indicated by arrow A. Proximal sliding motion of the sliding block 260 then causes the distal wall 272 to pull the tabs 236 of the two-piece hinged cap (220, 222) which causes the two-piece hinged cap (220, 222) to pivot about the attachment points (214, 216) of the introducer needle hub 26 as indicated by arrows B and B'. The sliding block 260 can advance until the two-piece hinged cap (220, 222) pivots 90 degrees relative to the closed position or until a medial surface 238 of the tabs 236 abuts against the outside surface 210 of the introducer needle hub 26, thereby serving as a hard stop. A fully open position as shown in FIG. 12 is defined by the medial surface 238 of the tabs 236 abutting against the outside surface 210 of the introducer needle hub 26.

In operation, a practitioner can pull the safety needle assembly 200 out of a package or kit, grasp the sliding block 260 and pull the sliding block 260 in a proximal direction until the safety needle assembly 200 is either in a fully open position or an intermediate position anywhere between the fully open and fully closed position. The safety needle assembly 200 can then be inserted into the skin of a patient and the desired medical procedure can be performed. Upon removal of the safety needle assembly 200, the safety needle assembly 200 can be withdrawn while simultaneously pulling the sliding block 260 in a proximal direction, thereby closing the two-piece hinged cap (220, 222).

As shown in FIG. 11A, the longitudinal length $L_W$ of the pair of wings 212, the distance $D_W$ (the distance between the distal edge 213 the pair of wings 212 and the distal end 30 of introducer needle hub 26) and the distance $D_B$ (the distance between the proximal wall 268 to the distal wall 272) can all be configured to limit the range of motion of the two-piece hinged cap (220, 222) as shown by arrows A, B and B' of FIG. 12.

Further embodiments are directed to a method of assembling a safety needle assembly 200 comprising the steps of attaching the two-piece hinged cap (220, 222) to the attachment points (214, 216) of the introducer needle hub 26, closing the two-piece hinged cap (220, 222), sliding the sliding block 260 absent the proximal wall 268 over the two-piece hinged cap (220, 222) until the distal wall 272 abuts the bottom surface of the tabs 236 of the two-piece hinged cap (220, 222), sliding the proximal wall 268 over the introducer needle hub 26 and securing or adhering the proximal wall 268 to the sliding block 260. In some embodiments, the method further comprises abutting the spinal needle hub 66 against the introducer needle hub 26 as previously explained.

Further embodiments are directed to a method of use of a safety needle assembly 200 comprising the steps of can pulling the safety needle assembly 200 out of a package or kit, grasping the sliding block 260 and pulling the sliding block 260 in a proximal direction until the safety needle assembly 200 is either in a fully open position or an intermediate position anywhere between the fully open and fully closed position. In some embodiments, the method further comprises the step of inserting the safety needle assembly 200 into the skin of a patient. In some embodiments, the method further comprises the steps of removing of the safety needle assembly 200 from the skin of a patient. In some embodiments the method further comprises the steps of pulling the sliding block 260 in a proximal direction, thereby closing the two-piece hinged cap (220, 222). In some embodiments, the method further comprises the steps of removing of the safety needle assembly 200 from the skin of a patient while simultaneously pulling the sliding block 260 in a proximal direction, thereby closing the two-piece hinged cap (220, 222).

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the disinfection cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Reference throughout this specification to “one embodiment,” “certain embodiments,” “one or more embodiments” or “an embodiment” means that a particular feature, structure, material, or characteristic described in connection with the embodiment is included in at least one embodiment of the disclosure. Thus, the appearances of the phrases such as “in one or more embodiments,” “in certain embodiments,” “in one embodiment” or “in an embodiment” in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A safety needle device assembly comprising:

an introducer needle having an introducer needle hub and an introducer needle cannula extending from a distal end of the introducer needle hub along a longitudinal axis of the introducer needle, the introducer needle hub having a pair of attachment points positioned at the distal end of the introducer needle hub;

a two-piece hinged cap having a medial portion, an elongated body, a proximal surface, and a distal surface configured to enclose at least the introducer needle cannula in a closed position of the two-piece hinged cap, the medial portion including a pair of tabs extending outward from the proximal surface in a direction transverse to the longitudinal axis in the closed position; and a sliding block configured to move the two-piece hinged cap between the closed position and an open position, the sliding block having a proximal wall, a distal wall and a sidewall therebetween defining a cavity, the proximal wall having an opening with a width which is less than a width of an opening in the distal wall, wherein the width of the opening in the distal wall is less than a total width of the pair of tabs, the distal wall configured to abut the pair of tabs.

2. The assembly of claim 1, further comprising a spinal needle having a spinal needle hub connected to the introducer needle hub.

3. The assembly of claim 2, wherein the medial portion is configured to cover and accommodate the connected introducer needle hub and spinal needle hub.

4. The assembly of claim 2, wherein the cavity of the two-piece hinged cap is a rectangular cavity having a length extending from a flange of the spinal needle hub slightly past the distal end of the introducer needle hub such that the introducer needle hub and spinal needle hub are fully enclosed within the rectangular cavity.

5. The assembly of claim 1, wherein the pair of attachment points creates a snap connection with the pair of corresponding attachment points.

6. The assembly of claim 1, the introducer needle hub further comprising a pair of wings extending from an outside surface of the introducer needle hub, the pair of wings having a width greater than the width of the opening of the proximal wall of the sliding block.

7. The assembly of claim 6, wherein the pair of wings are configured to interdigitate with a channel formed on an inside surface of the side wall of the sliding block.

8. The assembly of claim 6, wherein the pair of attachment points are positioned at a right angle relative to the pair of wings.

9. The assembly of claim 6, wherein the pair of wings has a longitudinal length configured to limit a range of motion of the two-piece hinged cap between the closed position and the open position.

10. The assembly of claim 1, wherein the proximal wall of the sliding block is removable from the sliding block.

11. The assembly of claim 1, wherein the medial portion of the two-piece hinged cap comprises a cut-out configured to permit a wider range of motion when opening the two-piece hinged cap.

12. The assembly of claim 1, wherein movement of the sliding block in a proximal direction is configured to cause the two-piece hinged cap to pivot about the pair of attachment points and open from the closed position to the open position.

13. The assembly of claim 1, wherein the two-piece hinged cap is injection molded forming a singular unitary body.

14. The assembly of claim 1, wherein the sliding block is configured to move the two-piece hinged cap from 0 degrees at the closed position to 90 degrees at the open position.

15. The assembly of claim 1, wherein the sliding block is configured to move the two piece hinged cap from the closed position to the open position until reaching a hard stop wherein a medial surface of the pair of tabs abuts against an outside surface of the introducer needle hub.

* * * * *